US005980973A

United States Patent [19]
Onyekaba et al.

[11] Patent Number: 5,980,973
[45] Date of Patent: Nov. 9, 1999

[54] IMPLANTABLE MEDICAL DEVICE WITH BIOCOMPATIBLE SURFACE AND METHOD FOR ITS MANUFACTURE

[75] Inventors: Chike O. Onyekaba, Brooklyn Park; George C. Johnstone, Brooklyn Center; David D. Verness, Forest Lake, all of Minn.

[73] Assignee: Medtronic, Inc., Minneapolis, Minn.

[21] Appl. No.: 09/042,289

[22] Filed: Mar. 13, 1998

[51] Int. Cl.⁶ ............................... A61F 2/02; B05D 5/02; B05D 1/38
[52] U.S. Cl. ......................... 427/2.24; 427/2.26; 427/189; 427/376.8; 427/405; 424/424; 606/60; 606/76; 623/1; 623/2; 623/11; 623/16; 623/901
[58] Field of Search ................................. 427/2.26, 2.24, 427/181, 189, 191, 376.7, 376.8, 405; 606/60.76; 424/424; 623/1, 2, 11, 16, 901

[56] References Cited

U.S. PATENT DOCUMENTS

| | | | |
|---|---|---|---|
| 4,101,984 | 7/1978 | MacGregor | 3/1.5 |
| 4,180,910 | 1/1980 | Straumann et al. | 433/173 |
| 4,206,516 | 6/1980 | Pilliar | 3/1.9 |
| 4,458,366 | 7/1984 | MacGregor | 3/1.1 |
| 4,483,678 | 11/1984 | Nishio et al. | 433/201 |
| 4,542,539 | 9/1985 | Rowe, Jr. et al. | 623/16 |
| 4,602,637 | 7/1986 | Elmqvist et al. | 128/419 P |
| 4,627,836 | 12/1986 | MacGregor | 604/93 |
| 4,846,834 | 7/1989 | von Recum et al. | 623/11 |
| 4,849,223 | 7/1989 | Pratt et al. | 424/409 |
| 5,011,494 | 4/1991 | von Recum et al. | 623/11 |
| 5,034,186 | 7/1991 | Shimammune et al. | 419/9 |
| 5,118,400 | 6/1992 | Wollam | 204/192.15 |
| 5,263,986 | 11/1993 | Noiles et al. | 623/16 |
| 5,368,881 | 11/1994 | Kelman et al. | 427/2.26 |
| 5,571,158 | 11/1996 | Bolz et al. | 607/121 |
| 5,673,473 | 10/1997 | Johnson et al. | 29/592.1 |
| 5,816,811 | 10/1998 | Beaty | 433/173 |

Primary Examiner—Diana Dudash
Attorney, Agent, or Firm—Reed A. Duthler; Harold R. Patton

[57] ABSTRACT

A method of providing biocompatible surface texturing on a metal component of an implantable device and the device so produced. The coating is provided by applying particles of metal falling substantially entirely in the range of 1 to 5 microns to a surface of said component to provide a layer of generally uniform thickness and sintering said particles to one another and to said component to provide a generally continuous external surface having surface texturing in the form of projections formed from said sintered particles. The particles are preferably applied to a depth of 1 to 25 microns. In a preferred embodiment particles of titanium are applied to a surface of a titanium component.

16 Claims, 3 Drawing Sheets

5,980,973

IMPLANTABLE MEDICAL DEVICE WITH BIOCOMPATIBLE SURFACE AND METHOD FOR ITS MANUFACTURE

BACKGROUND OF THE INVENTION

The present invention relates generally to implantable medical devices and more particularly to implantable medical devices having metallic components or enclosures, such as cardiac pacemakers, nerve stimulators, implantable drug dispensers, implantable defibrillators and the like.

In the context of implantable medical devices employing metallic enclosures or components, there have been numerous proposals for enhancing the biocompatibility of the surfaces of the enclosures or components. Typically, implantable electronic medical devices such as pacemakers, defibrillators, nerve stimulators or drug pumps, have enclosures fabricated of titanium or stainless steel. These enclosures are typically polished or bead blasted, as discussed in U.S. Pat. No. 5,673,473 issued to Johnson et al. In the context of other devices employing metal components, such as implantable heart valves and orthopedic prostheses, the use of porous sintered metal surfaces as disclosed in U.S. Pat. No. 4,206,516 issued to Pilliar and U.S. Pat. No. 4,101,984 issued to MacGregor is proposed. Such porous sintered surfaces are also suggested for a wide variety of other implantable devices, including artificial blood pumps, pacemaker electrodes, vascular access tubes, vascular grafts, and the like in U.S. Pat. Nos. 4,458,366 and 4,627,836, both issued to MacGregor. In these applications, the particle size is chosen to provide for an interconnected network of pores in the resulting sintered structure which are sized to permit ingrowth of soft or hard tissue, depending upon the application.

In the context of implantable pacemakers, cardioverters, defibrillators and other electronic stimulators, it has also been proposed to provide for porous, high surface area coatings such as porous sintered coatings in order to enhance the available surface area of the electrodes for enhanced electrical performance. For example, high surface area electrodes for location on electrical leads are discussed in U.S. Pat. No. 5,571,158 issued to Bolz et al, while high surface area electrodes forming a portion of the enclosure of an implantable stimulator are discussed in U.S. Pat. No. 4,602,637 issued to Elmqvist et al.

Recently, work done by Dr. Andreas Von Recum, as discussed in U.S. Pat. No. 5,011,494 and U.S. Pat. No. 4,846,834 suggests that soft tissue implant devices such as catheters, heart valves or reconstructive surgical material should be provided with a surface which has indentations or openings with bridging distances in the range of 1–4 microns, surrounded by solid surfaces having mean bridging distances in the range of 0.1–2 microns.

SUMMARY OF THE INVENTION

The present invention is directed toward the production of a biocompatible surface for use on metallic enclosures or metallic portions of implantable medical devices which coating encourages adhesion of tissue and does not produce an excessive inflammatory response. If the preferred embodiment of the invention comprises a component of the implantable device, manufactured of titanium or other biocompatible metal, and provided with a porous sintered coating fabricated of metal particles in the 1–5 micron range, preferably in the 1–3 micron range. The particles are preferably sintered to the metal surface in a thin layer to provide microscopic surface texturing, but are not intended to provide for a system of interconnected pores into which tissue may grow.

The titanium or other biocompatible metal component may take the form of all or a portion of the enclosure of a medical device or may also take the form of any other metal component of the device intended to contact body tissue directly, such as electrodes, sensors, prosthetic heart valves, housings and the like. The coating is preferably applied by spraying, painting, or by means of a syringe to produce 1–15 layers of the particles to provide a generally uniform coating thickness of 1–25 microns, and subsequently sintering the particles together to provide surface texturing, rather than interconnected porosity. Testing performed under the direction of the inventors has revealed that such surfaces provide a high degree of biocompatibility, promoting, good surface adhesion of tissue and a minimal inflammatory response.

DETAILED DESCRIPTION OF THE PREFERRED EMBODIMENT

Figure 1:
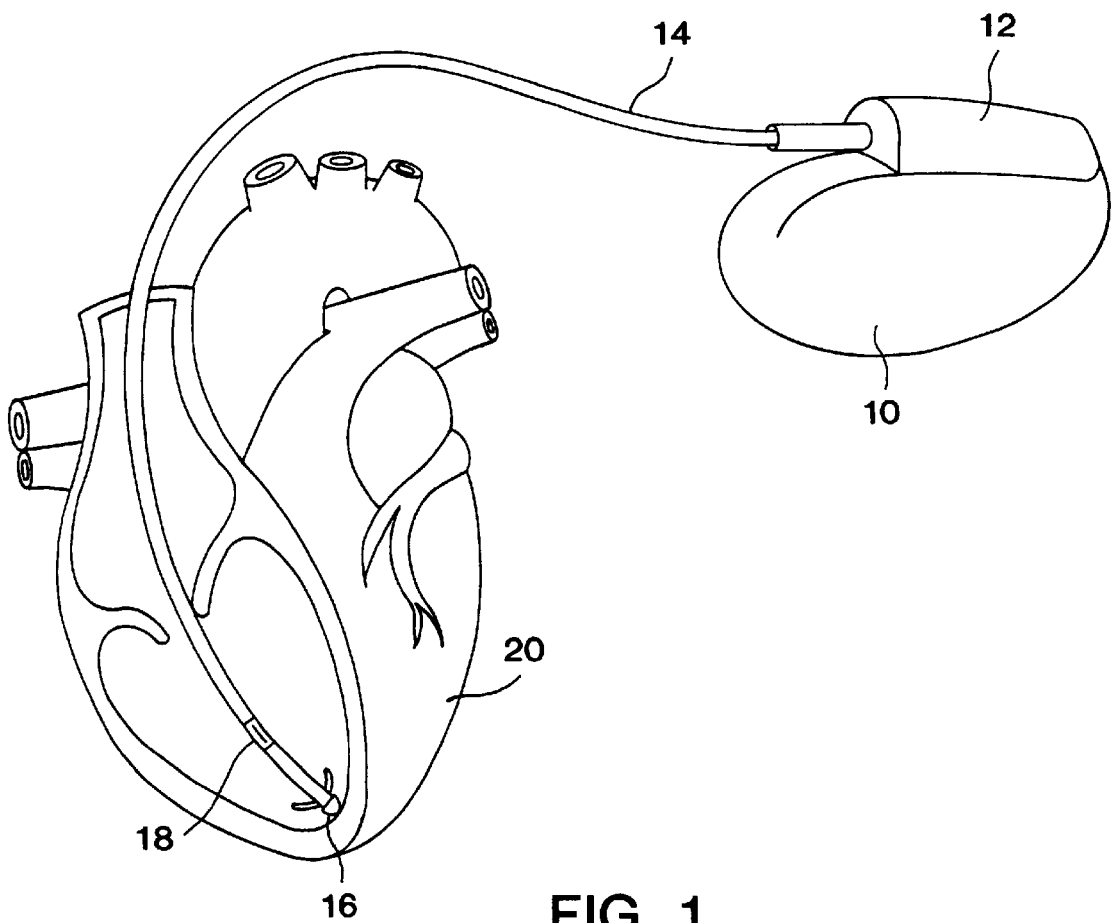
FIG. 1 is a drawing of an implantable medical device of the type in which the invention may be practiced.

FIG. 1 is a drawing of an implantable medical device of the type in which the invention may be practiced. In this case, the device illustrated is a cardiac pacemaker provided with a titanium housing 10 which contains a battery and associated electronic circuitry. A connector module 12 is coupled to the housing of the device, and is typically fabricated of epoxy or other plastic. Inserted into the connector block is a pacing lead 14, which is coupled to a pulse generator within the pacemaker, and serves to deliver pacing pulses to pacing electrodes 16 and 18 which may also be fabricated of a biocompatible metal and which may also employ a textured surface according to the present invention. In the context of the present invention, increased tissue adherence and a reduced inflammatory response adjacent the electrodes offers the opportunity for reduced pacing and sensing thresholds and a decreased incidence of microdislodgements.

Figure 2:
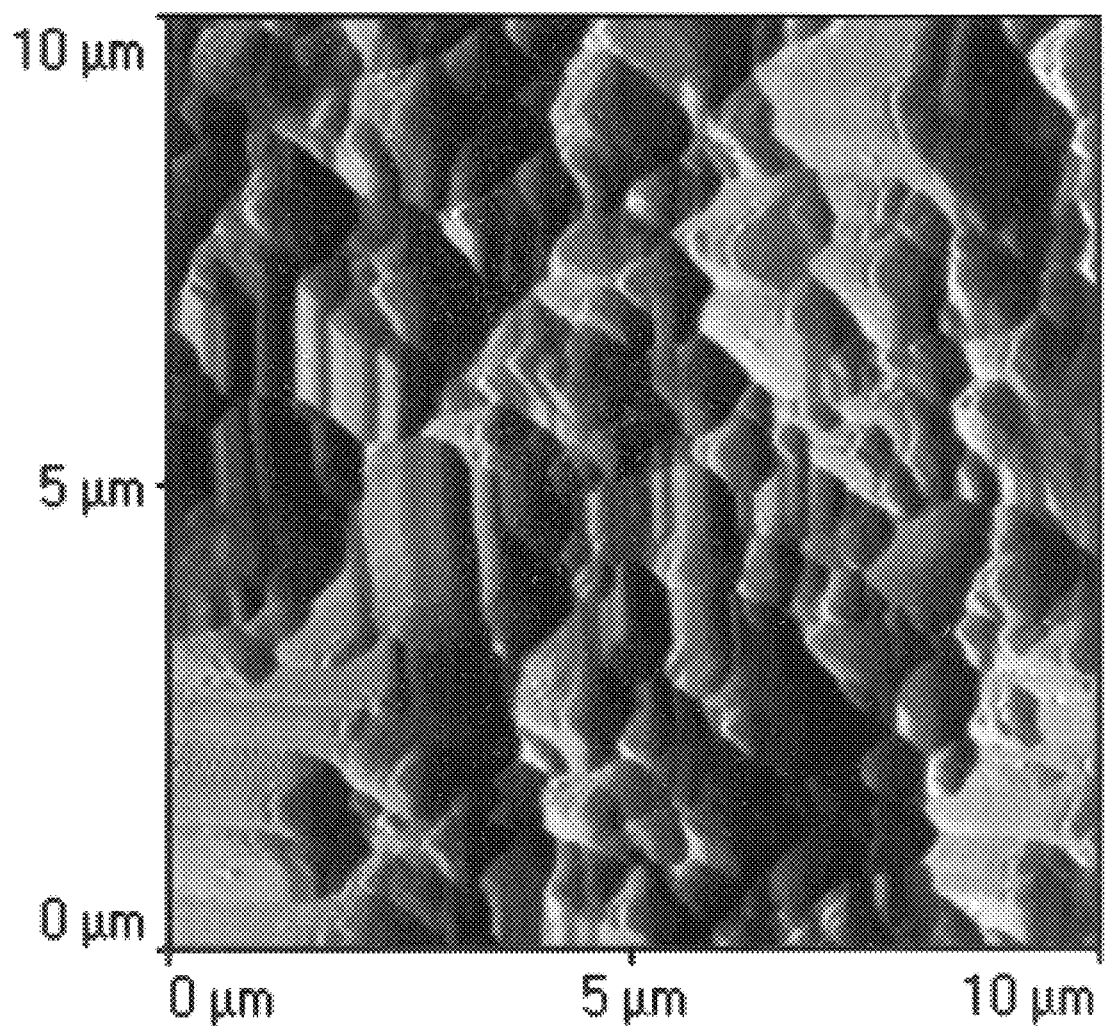
FIG. 2 is a drawing of a micrograph of a surface produced according to the present invention.

FIG. 2 is a drawing of a micrograph of a surface produced according to the present invention. The surface is produced by applying 1 to 5 micron particles of titanium, preferably 1 to 3 micron particles, to sheet titanium as might be found on the enclosure of an implantable medical device to a thickness of 1 to 25 microns and thereafter sintering the particles under vacuum in a radiant furnace to provide the coating as illustrated. The coating takes the form of a predominantly continuous surface provided with discreet projections formed from individual particles and from combinations of particles to produce an irregular, textured surface rather than a porous structure as in the above-cited Pilliar and MacGregor patents. The desired result is tissue adherence to the surface of the coating and improved biocompatibility, rather than cellular growth into the interior of a porous coating. Testing on behalf of the inventors has revealed that the surface as illustrated provides for increased adhesion of tissue and lower inflammatory response as compared to mirror polished titanium, titanium blasted with 440C stainless steel beads as in the above-cited Johnson et al patent and titanium ion beam etched to produce 0.03to 5 micron grooves, separated by 0.3 to 5 micron ridges. While the illustrated embodiment in FIG. 2 comprises a sintered coating applied to titanium sheet metal, it should be understood that the same sort of coating may be applied to other titanium substrates including machined solid bodies such as electrodes, heart valve housings and the like. Similarly, analogous coatings may be produced using other biocompatible materials such as vitalium, platinum or platinum alloys.

Figure 3:
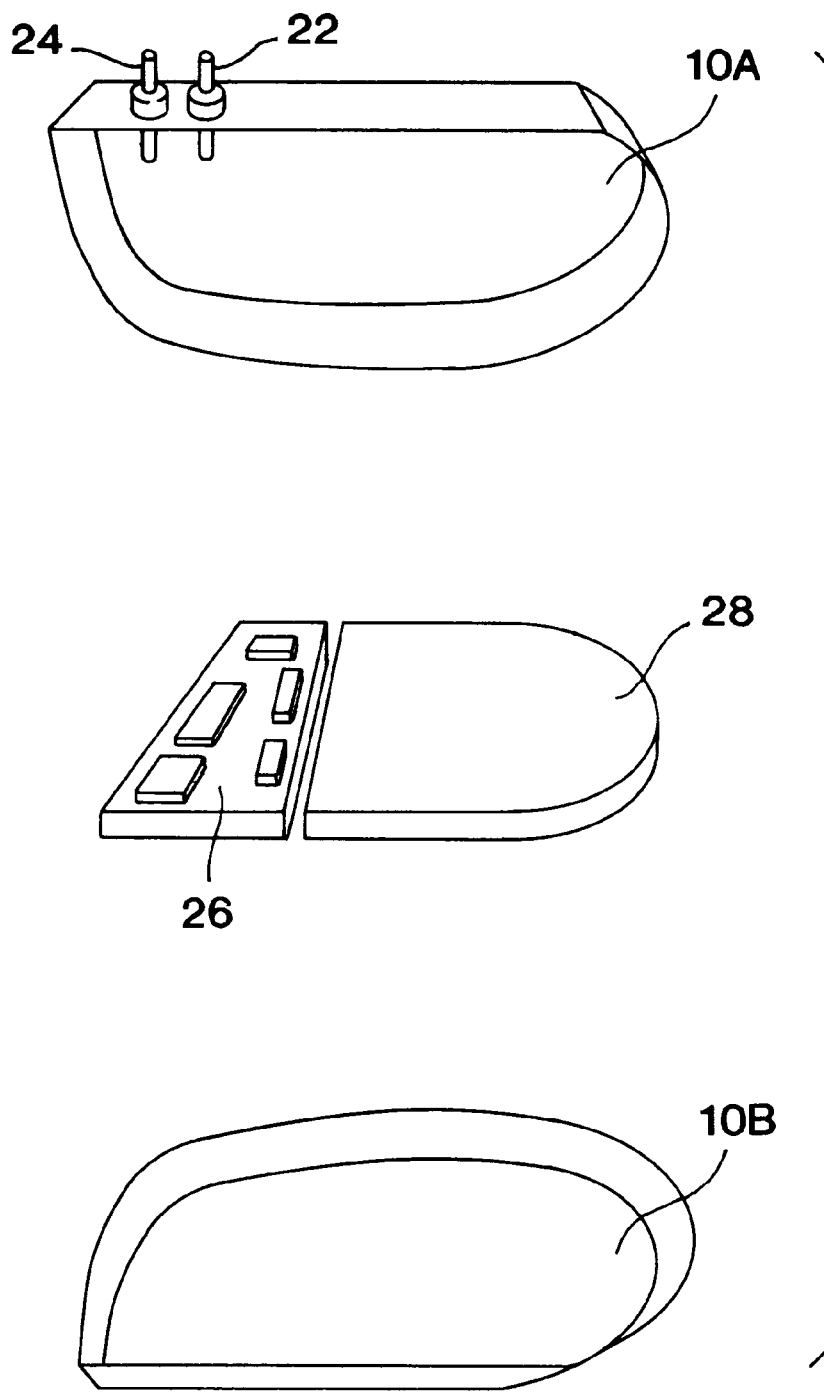
FIG. 3 illustrates the assembly of an implantable pacemaker as illustrated in FIG. 1, employing the present invention.

FIG. 3 illustrates the assembly of an implantable pacemaker as illustrated in FIG. 1, employing the present invention. The housing 10 (FIG. 1) is formed of two shield halves 10A and 10B, each of which are textured in part or in totality according to the present invention. Shield half 10A is provided with two feedthroughs 24 and 22 which serve to couple circuitry 26 to electrical connectors in the connector block 12 (FIG. 1). Shield halves 10A and 10B are laser welded together around their circumferences to provide a hermetic enclosure. As welding will disrupt the coating along the joined edges of the device, additional particles may be applied to the housing along the scam after initial welding and subsequently heated and sintered to the scam area by means of the same laser welder used to join the edges. The circuitry 26 is powered by means of a battery 28. The two shield halves 10A and 10B are attached to each other around their peripheries by laser welding, enclosing battery 28 and associated circuitry 26. Thereafter, connector block 12 is applied to the top of the device and electrical connectors located therein are coupled to feedthroughs 22 and 24, completing the assembly of the device.

In conjunction with the above disclosure, we claim:

1. A method of providing biocompatible surface texturing on a metal component of an implantable device, comprising:
   applying particles of metal falling substantially entirely in the range of 1 to 5 microns to a surface of said component to provide a layer of generally uniform thickness; and
   sintering said particles to one another and to said component to provide a generally continuous external surface having surface texturing in the form of projections formed from said sintered particles.

2. A method according to claim 1, wherein said applying step comprises applying particles to a depth of 1 to 25 microns.

3. A method according to claim 1 or claim 2 wherein said applying step comprises applying particles of titanium to a surface of a titanium component.

4. A method of fabricating an implantable medical device, comprising:
   selecting a metal enclosure for said device;
   applying particles of metal falling substantially in the range of 1 to 5 microns to a surface of said enclosure;
   sintering said particles to said component to provide surface texturing; and
   enclosing components of said device in said enclosure.

5. A method according to claim 4, wherein said applying step comprises applying particles to a depth of 1 to 25 microns.

6. A method according to claim 4 or claim 5 wherein said enclosing step comprises welding said enclosure.

7. A method according to claim 6, further comprising the step of sintering additional particles to said enclosure after said welding step, along a welded portion of said enclosure.

8. A method according to claim 4 or claim 5 wherein said selecting step comprises selecting a titanium enclosure and said applying step comprises applying particles of titanium to a surface of said titanium enclosure.

9. A metal component of an implantable device, having biocompatible surface texturing, made by the process of:
   applying particles of metal falling substantially entirely in the range of 1 to 5 microns to a surface of said component to provide a layer of generally uniform thickness; and
   sintering said particles to one another and to said component to provide a generally continuous external surface having surface texturing in the form of projections formed from said sintered particles.

10. A component according to claim 9, wherein said applying step comprises applying particles to a depth of 1 to 25 microns.

11. A component according to claim 9 or claim 10 wherein said applying step comprises applying particles of titanium to a surface of a titanium component.

12. A implantable medical device, fabricated by the process of:
   selecting a metal enclosure for said device;
   applying particles of metal falling substantially in the range of 1 to 5 microns to a surface of said enclosure;
   sintering said particles to said component to provide surface texturing; and
   enclosing components of said device in said enclosure.

13. A device according to claim 12, wherein said applying step comprises applying particles to a depth of 1 to 25 microns.

14. A device according to claim 12 or claim 13 wherein said enclosing step comprises welding said enclosure.

15. A device according to claim 14, further comprising the step of sintering additional particles to said enclosure after said welding step, along a welded portion of said enclosure.

16. A device according to claim 12 or claim 13 wherein said selecting step comprises selecting a titanium enclosure and said applying step comprises applying particles of titanium to a surface of said titanium enclosure.

* * * * *